(12) United States Patent
Palomino et al.

(10) Patent No.: US 7,275,499 B2
(45) Date of Patent: Oct. 2, 2007

(54) METHOD AND APPARATUS FOR THE IN-VITRO EVALUATION OF SUBSTANCES AS MOSQUITO REPELLENTS

(76) Inventors: Eduardo Palomino, 831 W. Farnum, Royal Oak, MI (US) 48067; Ann Sodja, 4302 Schafer Rd., Dearborn, MI (US) 48126

( * ) Notice: Subject to any disclaimer, the term of this patent is extended or adjusted under 35 U.S.C. 154(b) by 0 days.

(21) Appl. No.: 10/908,558

(22) Filed: May 17, 2005

(65) Prior Publication Data
US 2006/0260548 A1 Nov. 23, 2006

(51) Int. Cl.
*A01K 29/00* (2006.01)
(52) U.S. Cl. .................................. 119/6.5; 119/417
(58) Field of Classification Search .............. 119/6.5, 119/417, 416, 421; 43/107, 132.1; 514/919
See application file for complete search history.

(56) References Cited

U.S. PATENT DOCUMENTS

| | | | | |
|---|---|---|---|---|
| 2,244,082 A | * | 6/1941 | Reyniers | 600/21 |
| 3,580,219 A | * | 5/1971 | Stebbins | 119/6.5 |
| 3,874,335 A | * | 4/1975 | Galasso | 119/6.5 |
| 5,074,247 A | * | 12/1991 | Gupta et al. | 119/6.5 |
| 5,344,847 A | | 9/1994 | Wilson et al. | |
| 5,441,988 A | | 8/1995 | Butler et al. | |

* cited by examiner

*Primary Examiner*—T. Nguyen

(57) ABSTRACT

This invention provides an apparatus and a method for testing insect repellents that is derived from the behavior of mosquitoes in nature. The method is based on the displacement of mosquitoes from a place (cork) on a created habitat (corked-box) using a repellent substance. It does not require attractants, or blood-hungry mosquitoes, and it is appropriate for high throughput testing of different materials at the same time and in few hours.

1 Claim, 2 Drawing Sheets

Mosquito repellent testing chamber

Figure 1: Mosquito repellent testing chamber
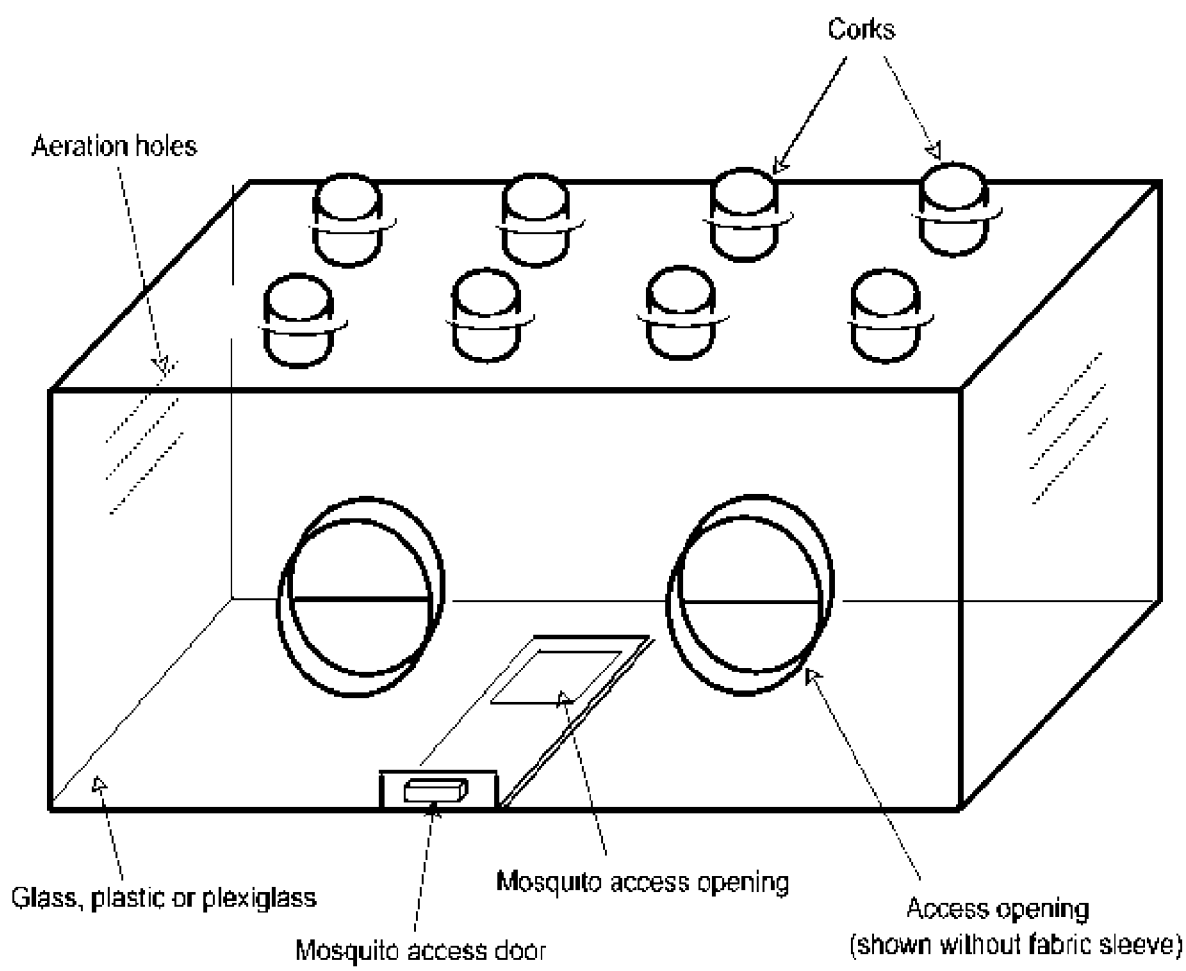

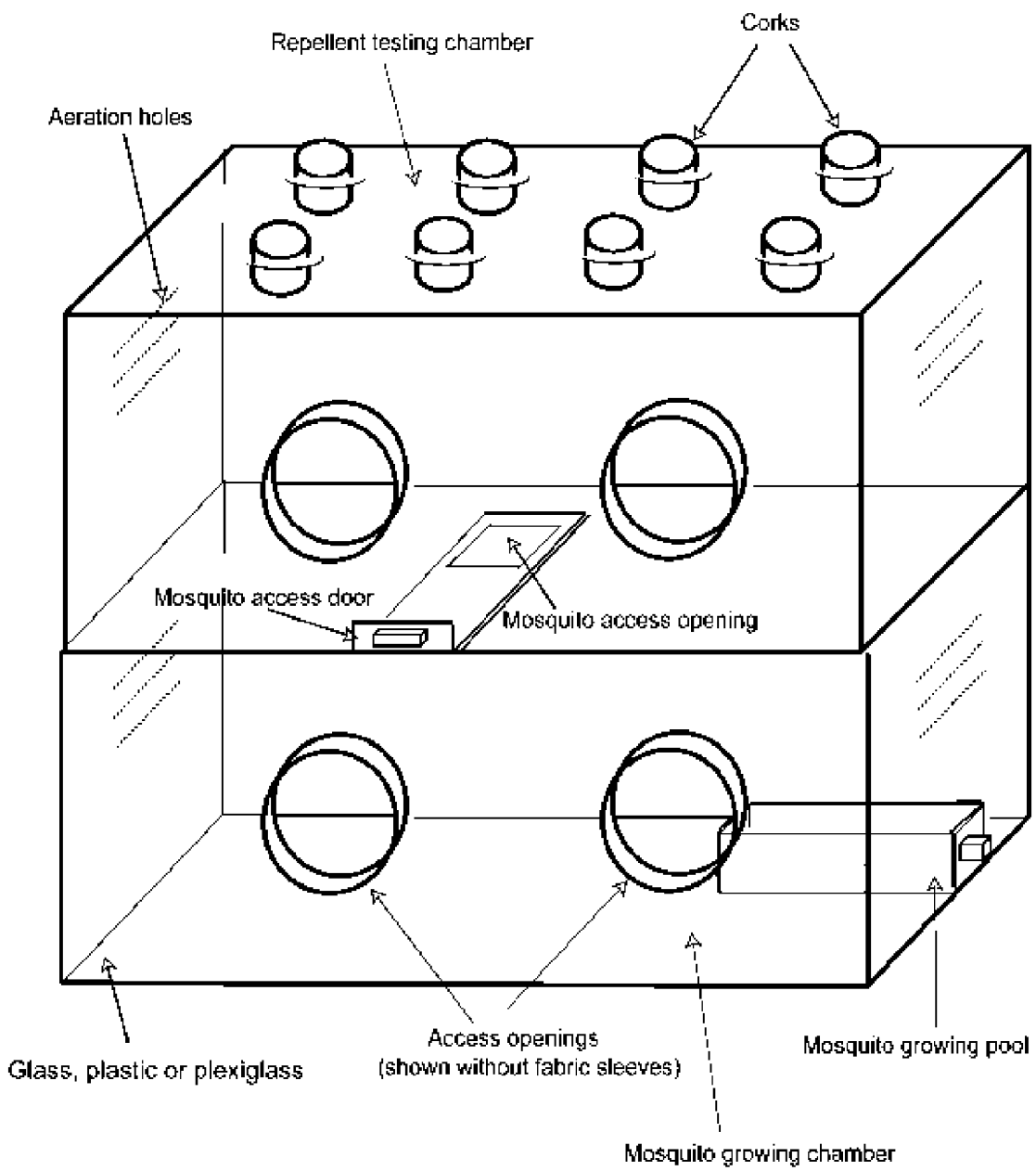
Fig 2. Mosquito repellent testing and growing chambers

METHOD AND APPARATUS FOR THE IN-VITRO EVALUATION OF SUBSTANCES AS MOSQUITO REPELLENTS

TECHNICAL FIELD

The present invention relates to an in-vitro method and an apparatus for evaluating the activity of any substance as a mosquito repellent. The method is particularly useful for screening a large amount of compounds in a short time and thus, is particularly suited for the development of new repellents through programmed studies of structure-activity models. The method does not have the limitations of the in-vivo method such as the level of hunger of the mosquitoes or the type of human or animal subject performing the test. Furthermore, the present invention provides a model apparatus in which the in-vitro tests can be performed and the requirements for such testing apparatus to work efficiently. Because the amounts of the testing materials are set in relation to a standard, the values of repellency are repetitive, eliminating discrepancies in different tests.

BACKGROUND

Despite the prevalence of mosquito-transmitted diseases such as malaria and dengue, little progress has been made in the development of a safe mosquito repellent. In the middle of last century a large number of compounds were evaluated in-vivo for repellency against *Aedes aegypti*(the yellow fever mosquito) and other species of blood-sucking mosquitoes. The study was a large random search through a variety of chemical structures, most of them organic, which provided several potential compounds for development. From these studies, the most popular mosquito repellent today, N,N-diethyl-m-toluamide (DEET, or m-DEET), emerged first for the use of the US Army and later for use of the general public. A few animal studies on DEET have shown a range of toxic effects ranging from skin irritation to adverse neurological effects. Other compounds, natural and synthetic, have been used but due to their range of action and level of safety have had little success compared to DEET.

The development of safe repellents has been hampered by the poor knowledge of the mosquito's receptors and the difficulties involved in the testing of new substances. In addition to the lack of molecular targets (receptors) for rational design, the testing of new chemicals as potential repellents using humans is variable and intrinsically dangerous, since the toxicology of the new substance is usually not known. The in-vivo test in practice today dates back to 1919 and uses the forearm or the hand of human subjects exposed at short time intervals to hungry mosquitoes. Other methods have been tried in order to overcome the shortcomings of the human test but none have prevailed due to the fact that most of them rely on the attractants of an animal subject and the need of a hungry female mosquito. Reliability of the human test is questionable. Early verification of the activity of DEET, for instance, gave zero activity in the first test using the arm, lasted 2 h in a Russian measurement using the forearm, and 5 h using a hand test. Number and degree of hunger of the mosquitoes, concentration of the repellent, and differences in the type of attractants released by the human subjects can account for the discrepancies. Furthermore, because the method is based on the attractants released on the skin, the human test cannot distinguish between substances that actually affect the sensory system of the insect (true repellents) and those that block the release of those attractants from the skin (attractant blockers).

There is therefore a need to develop a better testing method for the evaluation of mosquito repellents such as the one described here. This new approach overcomes the limitations of the human method by not relying on the attractants present in the human skin or on the need of the female mosquito of a blood meal. Thus, this method differentiates between true repellents and attractant blockers. This method is based on the disturbance created by the repellent of the natural tendency of the mosquito to rest in certain rough surfaces above ground.

SUMMARY

The present invention recognizes the need to rapidly and reliably evaluate potential mosquito repellents of unknown nature, man-made or nature-derived. It also recognizes that an effective testing method should take into account the potential human toxicity of the unknown materials tested. Thus, the present invention recognizes that no humans or animals should be involved as subjects in the testing to eliminate the potential toxicity of the unknown materials tested on them. The present invention also recognizes that such method should be reliable and repetitive under a set of standard conditions given and not be dependent on mosquito attractants or on the need of the mosquitoes for a blood meal. The present invention permits the identification of unknown materials useful as mosquito repellents, does not require attractants from humans or blood-hungry mosquitoes, and it permits the evaluation of a large number of compounds in few hours. The present invention thus provides unique advantages over the most commonly used human forearm method. It is fast, safe, simple and reliable and provides a foundation of standards that anybody can duplicate and evaluate.

BRIEF DESCRIPTION OF THE FIGURES

FIG. 1. Drawing of the box or chamber used for the in-vitro testing of mosquito repellents. The drawing shown displays 8 corks atop a transparent smooth box where the repellent substances are impregnated. The box also has two access openings on the front which under working conditions are covered with a fabric sleeve. These access openings are used to introduce water and food for the mosquitoes as well as for performing cleaning of the box. Also shown is an access opening at the bottom with a door for the introduction of mosquitoes grown in a separate cage, and aeration holes on the side panels.

FIG. 2. Drawing of a transparent chamber used for the in-vitro testing of mosquito repellents atop a mosquito growing chamber. The repellent testing chamber on top displays 8 corks where the repellent substances are impregnated. The mosquito growing chamber displays a mosquito growing pool at the bottom where mosquito eggs are developed into adult mosquitoes. Both chambers display access openings used for the introduction of water and food as well as for performing cleaning of the boxes. The bottom of the repellent testing chamber displays an access opening with a door for the introduction of the mosquitoes grown in the bottom chamber

DETAILED DESCRIPTION OF THE INVENTION

The natural tendency of the most routine testing mosquito model, *Aedes aegypti*, is to rest on the walls and ceiling of the common laboratory wire mesh cage rather than to stand on the bottom. This tendency is observed in many mosquito species. When the surfaces of walls and ceiling of the cage are changed to smooth and polished—such as acrylic plastic or glass—, the insects are forced to rest on the bottom. If a rough surface is provided on the ceiling of that smooth box, that rough surface becomes the preferred resting place for the mosquitoes. It is on the above observations that the present method is based.

The following description of the bioassay uses definite dimensions and materials for the corked-box; however, other dimensions and materials can be used according to the needs. To perform the bioassay, a 2 ft×1 ft×1 ft box, such as the one depicted in FIG. 1, is built of plexiglass with minute aeration holes on the side panels, 8 holes (1.5 inches diameter each, 6 inches apart from each other) on the top to accommodate as many #21 cork stoppers. Two larger holes (4 inches diameter) on the front panel fitted with a cotton sleeve for easy hand access, and a 4 inch square mosquito access opening with door at the bottom completes the box design. Food (10% sucrose) and water are provided inside the box in two small Erlenmeyer flasks with cotton wicks. Under normal conditions, when the box is filled through the mosquito access opening, with about 400 mixed-sex mosquitoes, 20 to 40 will rest on each cork. Thus, the size of the corks and the number of mosquitoes per cubic feet are important for the test to be statistically significant. The cork material is not an attractant; a cork sitting at the bottom of the cage does not attract mosquitoes. The design of this box and testing conditions permits the evaluation of 8 substances at the same time with no crossover effect from one cork to its neighbors. When a cork impregnated with a repellent is replaced with a new cork, mosquito landing on the new cork is immediate. Thus, testing can be performed continuously on different compounds.

Repellent testing is performed with mosquitoes 3 days to 3 weeks old that are maintained at 70–80% humidity and a temperature of 27–29° C. with an artificial 16—8 day-night cycle. On average 200–300 mosquitoes per cubic foot provide optimum results. Substances to be tested are prepared at a concentration 0.015 M in ethanol. This concentration is important because 1) the activity of repellents is directly proportional to concentration and 2) for relative comparison to the standard DEET. A cork impregnated with a solution of DEET at that concentration (0.015 M) produces a Repellence Time (RpT) of about 4 h. Repellency Time (RpT) is defined as the time between the introduction of an impregnated cork into the testing chamber and the time one mosquito lands and remains on that cork for 1 minute.

In a typical experiment, a cork is immersed for 30 seconds in an ethanol solution of the compound under study at a concentration of 0.015 M. The alcohol is allowed to evaporate (about 10 min.) and the cork is inserted into one of the top holes of the testing chamber that contains between 200 and 300 mosquitoes per cubic foot. The time is recorded and the cork is observed directly by a technician or monitored by a video camera connected to recorder for later evaluation. The presence of one mosquito on the cork for 1 minute determines the end of the test, and the repellency time (RpT) is then noted. The area of substance coverage on the cork is about 30 $cm^2$, and the amount of substance on the cork after evaporation of the alcohol is about 7.7×10-4 $mmol/cm^2$. Blank corks are immersed in pure ethanol for the same amount of exposure and evaporation times. However, blank corks are not required except to verify that the alcohol does not contain repellent substances as contaminants.

The following comparison of repellencies was made between reported in-vivo values from different sources and those obtained using the in-vitro method presented here. The list shows that a correlation exists between the two methods and that the in-vitro method can be used to predict the repellency time of a given repellent in humans. Compounds o-DEET, m-DEET, and p-DEET correspond to the three isomers of the same material; the m-DEET is the most active and it is the one used as the standard.

| Compound | RpT (min) in-vivo | RpT (min) in-vitro |
|---|---|---|
| o-DEET | 90 | 20 ± 5 |
| m-DEET | 300 | 240 ± 20 |
| p-DEET | 240 | 210 ± 20 |
| Camphor | 0–60 | 15 ± 2 |
| Geraniol | 120–180 | 315 ± 20 |
| Nerolidol | 120–180 | 300 ± 25 |
| Citronellal | 0–60 | 0 ± 5 |
| 2-Tridecanone | 0–60 | 20 ± 5 |
| Amyl alcohol | 0–60 | 5 ± 1 |
| Cyclohexanol | 0–60 | 10 ± 1 |
| Cyclohexanone | 0–60 | 0 |
| Oleic acid | 0–60 | 0 |

REFERENCES

Abdel-Rahman, A., Shetty, A. K., Abou-Donnia, M. B. (2001) Sub-chronic dermal application of N,N-diethyl m-toluamide (DEET) and permethrin to adult rats, alone or in combination, causes diffuse neuronal cell death and cytoskeletal abnormalities in the cerebral cortex and the hippocampus, and Purkinje neuron loss in the cerebellum. Experimental Neurology. 172: 153–171.

Fradin, M. S., Day, J. F. (2002) Comparative efficacy of insect repellents against mosquito bites. New Eng. J. Med. 347: 13–18.

King, W. V. (1954) Chemicals evaluated as insecticides and repellents at Orlando, Fla. USDA Agriculture handbook No 69.

Knippling, E. F., Mcalister, L. C., Jones, H. A. (1947) Results of screening tests with materials evaluated as insecticides, miticides, and repellents at the Orlando, Fla., laboratory. April 1942 to April 1947. USDA Publication E-733.

Ma, D. A., Apurba, K., Bhattachariee, R., Gupta, K., Karle, M. J. (1999) Predicting mosquito repellent potency of N,N-dietyl-m-toluamide (DEET) analogues from molecular electronic properties. Am. J. Trop. Med. Hyg. 1–6.

Schreck, C. E. (1977) Techniques for the evaluation of insect repellents: a critical review. Ann. Rev. Entom. 22: 101–119.

Suryanarayana, J. V. S., Pandey, K, S., Prakash, S., Raghuveeran, C. D., Dangi, R. S., Rao, K. M. (1991) Structure-activity relationship studies with mosquito repellent amides. J. Pharm. Sc. 80: 1055–1057.

Vogt, R. G. (2003) Biochemical diversity of odor detection: OBPs, ODEs and SNMPs. p. 391, in G. J. Blomquist and R. G. Vogt (eds.). Insect pheromone biochemistry and molecular biology: the biosynthesis and detection of pheromones and plant volatiles. Elsevier Academic, London.

Zolotarev, E. K., Kalakustkaya, T. V. (1962) Repellent study IX. Diethyltoluamides. Comparative evaluation of ortho-, meta- and para-isomer repellency against ticks and mosquitoes. Vestn. Mosk. Univ. 3: 18–21

What is claimed is:

1. A method of testing mosquito repellents in which mosquitoes standing on a plurality of corks in an apparatus, wherein said apparatus consisting of a transparent aerated box of smooth surfaces having a plurality of holes on a top surface, a plurality of corks affixed on said plurality of holes, access openings on a front surface protected with fabric sleeves, and an access opening on a bottom surface for mosquitoes introduction, the method comprising the steps of:

(i) introducing said transparent aerated box with at least 400 mosquitoes;

(ii) impregnating said plurality of corks with a 0.015 molar ethanolic solution of repellent substance; and then (iii) measuring the length of time mosquitoes remain away from said impregnated plurality of corks, said length of time is defined as a repellence time wherein said repellence time is a time between the introduction of said impregnated plurality of corks into said transparent aerated box and the time at least one mosquito lands and remains on said cork for 1 minute.

* * * * *